United States Patent [19]
Smith, deceased et al.

[11] 3,978,864
[45] Sept. 7, 1976

[54] ELECTROTHERAPEUTIC TREATMENT HEAD

[75] Inventors: Luther B. Smith, deceased, late of Miami Beach, Fla., by William F. L. Fry, and Richard E. Jordan, executors

[73] Assignee: L. B. Smith Estates, Inc., Washington, D.C.

[22] Filed: Nov. 17, 1966

[21] Appl. No.: 600,341

Related U.S. Application Data

[63] Continuation-in-part of Ser. No. 552,999, April 29, 1966, abandoned, which is a continuation-in-part of Ser. No. 494,511, Oct. 11, 1965, abandoned.

[52] U.S. Cl. ............................................. 128/404
[51] Int. Cl.² .......................................... A61N 1/40
[58] Field of Search .......... 128/404, 405, 413, 421, 128/422; 336/129, 209, 223, 231

[56] References Cited
UNITED STATES PATENTS

| | | | |
|---|---|---|---|
| 2,549,399 | 4/1951 | Tawney | 128/413 |
| 2,583,854 | 1/1952 | Kehbel | 336/231 X |
| 2,695,021 | 11/1954 | Touzel | 128/422 X |
| 3,043,310 | 7/1962 | Milinowski | 128/422 |
| 3,270,746 | 9/1966 | Kendall et al. | 128/404 |

FOREIGN PATENTS OR APPLICATIONS

| | | | |
|---|---|---|---|
| 40,032 | 7/1887 | Germany | 128/413 |
| 954,128 | 4/1964 | United Kingdom | 128/405 |

*Primary Examiner*—William E. Kamm
*Attorney, Agent, or Firm*—Cushman, Darby & Cushman

[57] ABSTRACT

An electrotherapeutic treatment head is disclosed for use with a drive circuit which applies pulses of electrotherapeutic energy to the treatment head. The head includes a hollow housing in which is mounted a spiral coil, the coil being flat in the plane of the spiral. Connected to the coil is an adjustable capacitor, one plate of the capacitor being connected to one of the outer loops of the spiral-shaped coil while the other plate thereof is connected to one of the inner loops. The capacitor and coil together form a tank circuit. Also disposed in the housing is a primary coil which is directly connected to the drive circuitry and which inductively couples the pulsed energy to the spiral-shaped coil, from whence it is radiated to an appropriate load such as a patient. The primary coil consists of a single loop and is flat in the plane of the loop and parallel to the spiral-shaped coil.

Also disclosed are various modifications of the spiral-shaped coil, the primary coil, and means for mounting the primary and spiral-shaped coils within the housing.

15 Claims, 20 Drawing Figures

INVENTOR
LUTHER B. SMITH

BY
Cushman, Darby & Cushman
ATTORNEYS

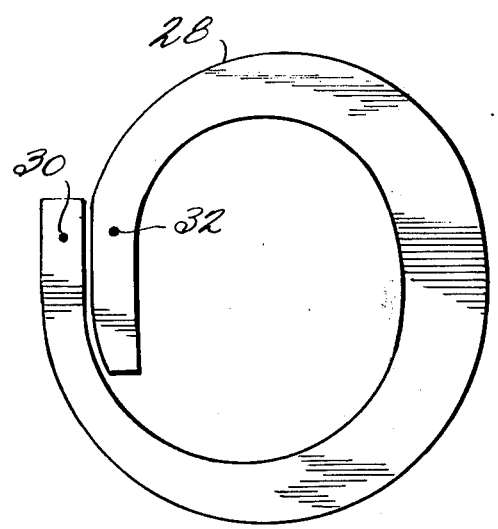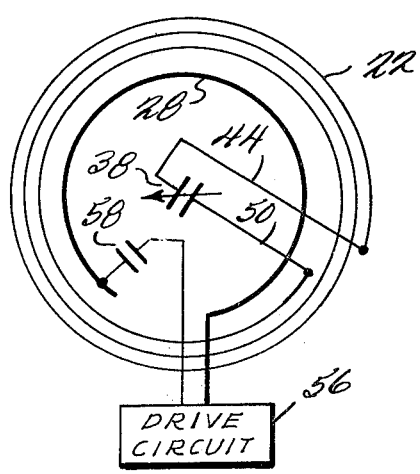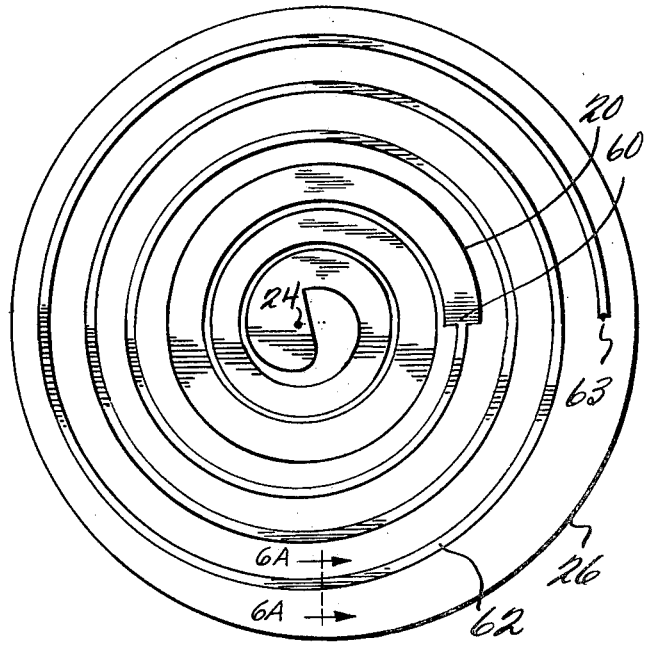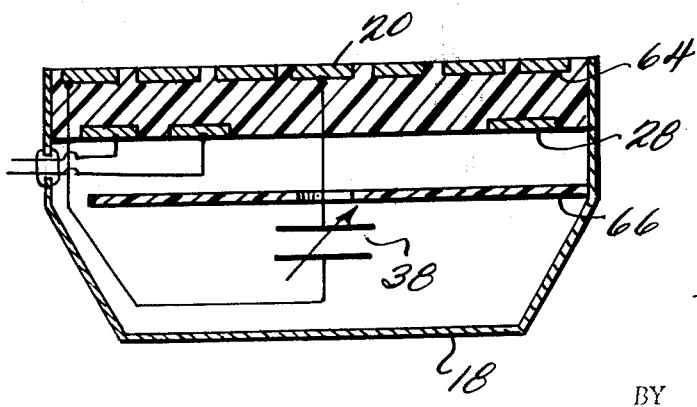

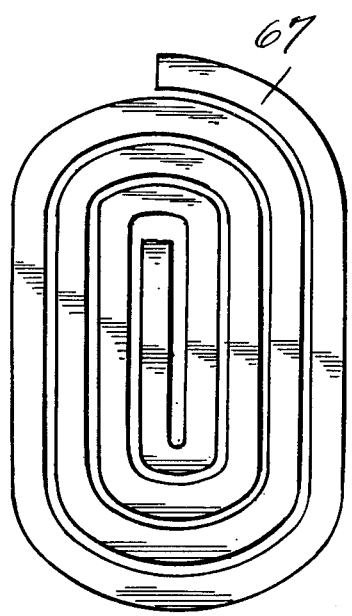
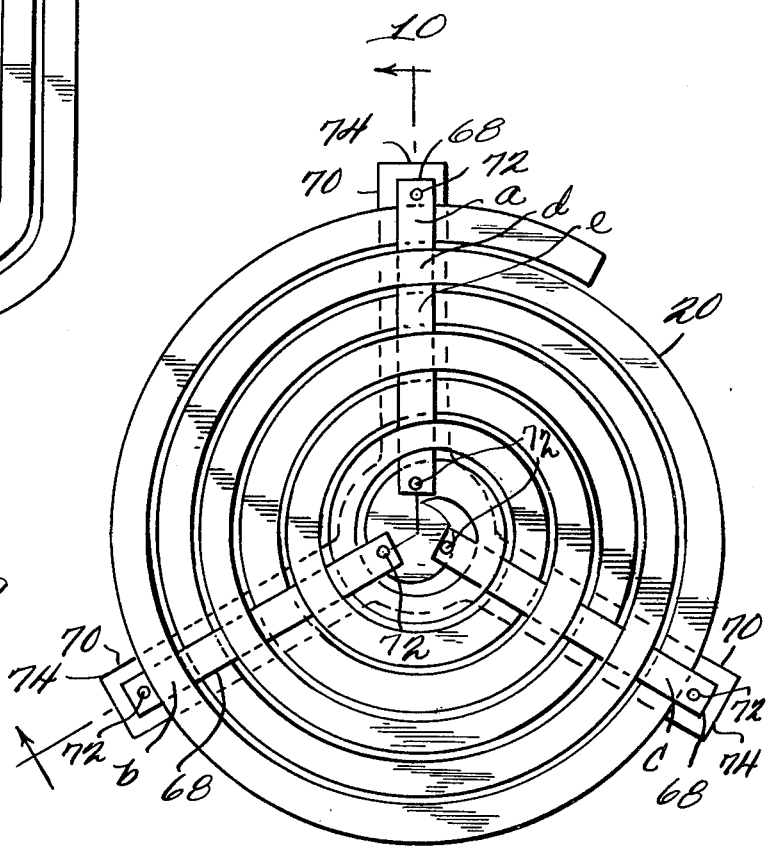
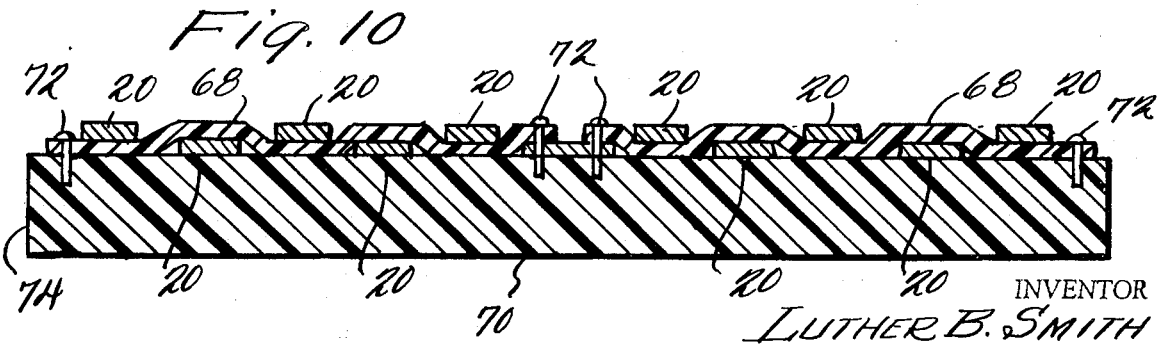

INVENTOR
LUTHER B. SMITH

BY Cushman, Darby & Cushman
ATTORNEYS

INVENTOR
LUTHER B. SMITH

BY Cushman, Darby & Cushman
ATTORNEYS

ELECTROTHERAPEUTIC TREATMENT HEAD

This application is a continuation-in-part of Applicant's copending Application Ser. No. 552,999 which is a continuation-in-part of Applicant's copending Application Ser. No. 494,511, entitled ELECTROTHERAPEUTIC TREATMENT HEAD and filed Oct. 11, 1965 both now abandoned.

This invention relates generally to treatment heads used with electrotherapeutic apparatus and, more particularly, this invention relates to improved conductor or radiating elements disposed within the treatment head for improving the effectiveness of the electromagnetic energy delivered by the electrotherapeutic apparatus to the treatment head.

Further, this invention relates to improved treatment heads which are compact in size and easily manipulated.

As is well-known in this art, a thermapeutic apparatus may be employed to provide therapeutic treatments to various types of living or organic matter or tissue. This apparatus typically comprises a primary coil connected to a source of pulsed, electromagnetic energy, the primary coil coupling energy to a tuned secondary circuit which is placed in juxtaposition to the area to be treated. Especially the treatment of a diseased or infected portion of the human body can be effectuated by applying pulsed, electromagnetic energy to the particular portion in need of treatment. The ratio of off time to on time is usually kept large, thereby insuring effective treatment with a pulse having a large amount of energy contained therein while at the same time insuring that treated portion does not overheat or burn.

In prior art devices, it has been observed that when the diseased or infected area is well beneath the surface of the skin, satisfactory treatment is not obtained. Although the theory of operation of the present invention is not fully understood, it has been observed that deeper penetrations of the treated matter are possible or more effective treatment is possible at deeper levels.

Further, it has been observed in prior art electrotherapeutic devices that when the peak power in a given pulse of energy is increased beyond a certain point, that undue heating and perspiration occur. Because of the danger of the perspiration turning to steam and burning the patient, the prior art devices are operated well within certain maximum limitations on the peak power to insure the patient's safety. However, it has been found that the peak power limit is significantly increased by utilizing the improved treatment head of the present invention. Possibly this result is obtained by spreading out in space the energy contained within a given pulse to thereby reduce heating effects at a particular localized area of the treated matter.

It has also been observed with prior art treatment heads that satisfactory treatment is not obtained when a small, localized area is treated. For instance, if a small area or spot at the wrist is in need of treatment, the prior art devices have not proved effective in treating such areas.

Another disadvantage of prior art treatment heads results from their bulkiness or size — that is, it is sometimes desirable to manually place and hold the treatment head at an area of the body which is difficult to reach; however, because of the large size and bulkiness of the prior art treatment heads, it is often impractical or very inconvenient to place and hold the treatment head at such locations. The bulkiness of prior art treatment heads results from a disadvantageous arrangement of electrical components within the head. This problem is overcome by the compact treatment head taught by this invention.

Yet another disadvantage results from the prior art devices because circular treatment heads are employed. This also results in the inability of the patient or equipment operator to place the head at difficult-to-reach areas of the body. Of course, many applications of this invention do not require the patient or operator to place the treatment head at difficult-to-reach areas. In such applications, it will still be desirable to employ the aspects of this invention which increase the effectiveness of the applied radiation.

Accordingly, it is an object of the invention to provide increased effectiveness upon treated matter or organic tissue, while at the same time significantly decreasing the heat generated within the said matter.

It is another object of the invention to provide a compact treatment head which is readily handled by the patient or operator of the electrotherapeutic apparatus.

It is another object of the invention to provide an improved treatment head for treating small, localized diseased or infected areas of matter.

It is another object of the invention to provide a treatment head of convenient shape for treating hard-to-reach areas of the human body.

It is another object of this invention to provide improved primary and secondary coils for use in an electrotherapeutic treatment head.

A brief description of an illustrative embodiment of the invention for carrying out the above-mentioned objects will now be given.

The electrotherapeutic apparatus supplies the treatment head with pulsed electromagnetic energy. The treatment head comprises a hollow housing within which is mounted trensformer means comprising primary conductor means and a secondary circuit comprising a conductor or radiating coil and a tunable condenser preferably of the parallel plate type. The energy delivered from the electrotherapeutic apparatus drives the primary coil. The primary coil couples energy to the coil in the secondary circuit, said secondary circuit being further loaded by the treated portion of the patient or other treated matter.

The housing may have a central axis or other axis about which the primary coil may be centered. It follows that this axis has no preferred orientation within the housing. The secondary coil spirals about this axis and is constructed so that at least a portion of the coil conductor is flat in the plane of the spiral. This coil extends approximately from the axis itself outwardly to the periphery of the housing and is normally in juxtaposition with respect to the treated matter, thereby facilitating the transfer of electromagnetic energy thereto. This is one of the features which affords novelty and utility. It is not critical that the flat conductor extend all the way to the periphery and, in some instances, the flat conductor may extend from the axis to a point intermediate the axis and periphery of the housing, the remaining portion of the secondary conductor or radiating element comprising a solid or tubular wire which completes the spiral of the secondary to the periphery. Of course, the important thing is to insure a wide or flat conductor spiral at some portion along the radial extending from the axis, this portion corresponding to the area which is to be treated. Further, if only a portion of the secondary spiral is flat, it follows that it is not necessary that the secondary conductor continue to be a spiral to either the axis or the periphery. Rather, the ends of the flat spiral can be terminated in any number of different ways which will occur to one having ordinary skill in this art.

The primary coil may also be a flat conductor as is the secondary. Adjustment of the spacing between the primary and secondary may be provided to maximize the beneficial effects for a particular patient.

The tuning condenser within the secondary circuit, as mentioned above, may be so oriented within the housing that its plates are parallel with respect to the plane of the spiral of the secondary coil and the loop of the primary coil, thereby providing a compact treatment head suitable for easy manipulation by the patient or operator of the treatment head. To reduce undesirable interaction between the tuning condenser when it is so oriented and the primary and secondary coils, a metallic partition must be placed within the housing physically separating the condenser from the coils. This undesirable interaction may also be reduced by employing a cylindrical, piston, piston-type tunable condenser.

If a particular situation warrants a fixed spacing between the secondary and primary coils, the primary and secondary coils can be produced on the opposite sides of a dielectric laminate by printed circuit techniques. Further, the primary and secondary can be produced on separate dielectric lamina whenever it is desired that the spacing between the primary and secondary be varied.

A more detailed description will now be given of an illustrative embodiment of the invention, referring when necessary to the drawing where:

FIG. 1 diagrammatically illustrates a prior art treatment head showing the placement of the radiating or conductor coils with respect to housing therefor;

FIG. 4 is a top view of an illustrative embodiment of the primary coil of the treatment head;

FIG. 5 is a schematic diagram illustrating the connections between the various electrical elements of a complete electrotherapeutic apparatus and treatment head;

FIG. 6 is a top view of a modification of the conductor means shown in FIG. 3;

FIG. 6A is a cross-section taken along the line 6A—6A of FIG. 6.

FIG. 7 is an elevation taken in section through another embodiment of an electrotherapeutic treatment head;

FIG. 8 is a diagrammatic presentation of an oblong shaped conductor means or radiating coil employed in a further embodiment of the invention;

FIG. 9 is a top view of a diagrammatic representation of a support structure for the conductor means;

FIG. 10 is a section view of the structure shown in FIG. 9 along the line 10—10;

Figure 12:
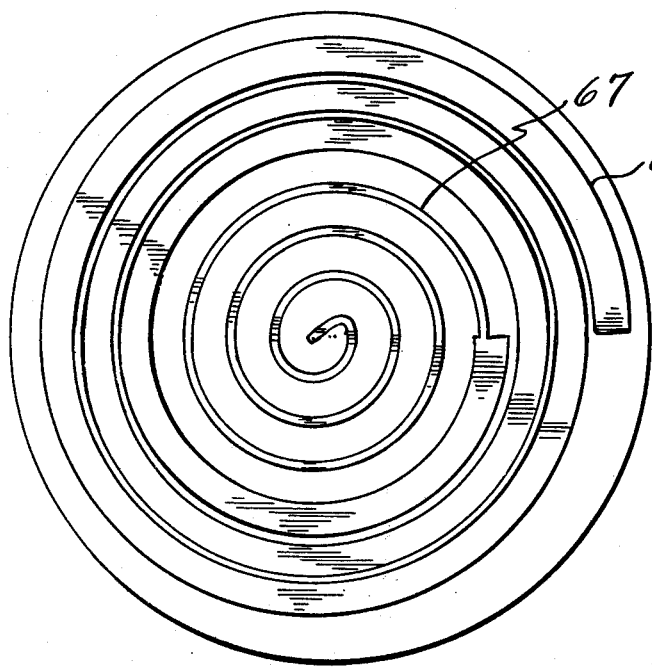
FIG. 12 is a further modification of the conductor means shown in FIG. 3.
Figure 13:
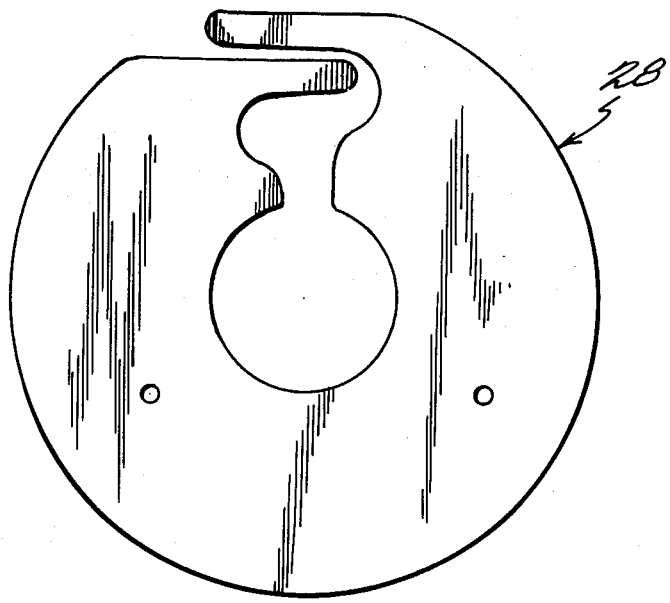
Figure 14:
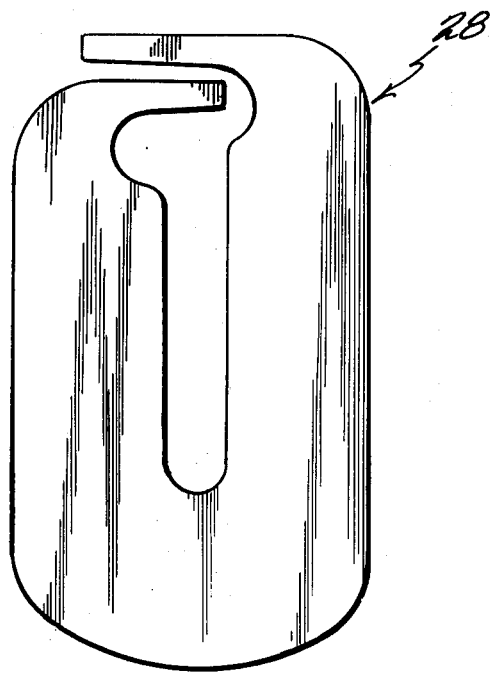
Figure 15:
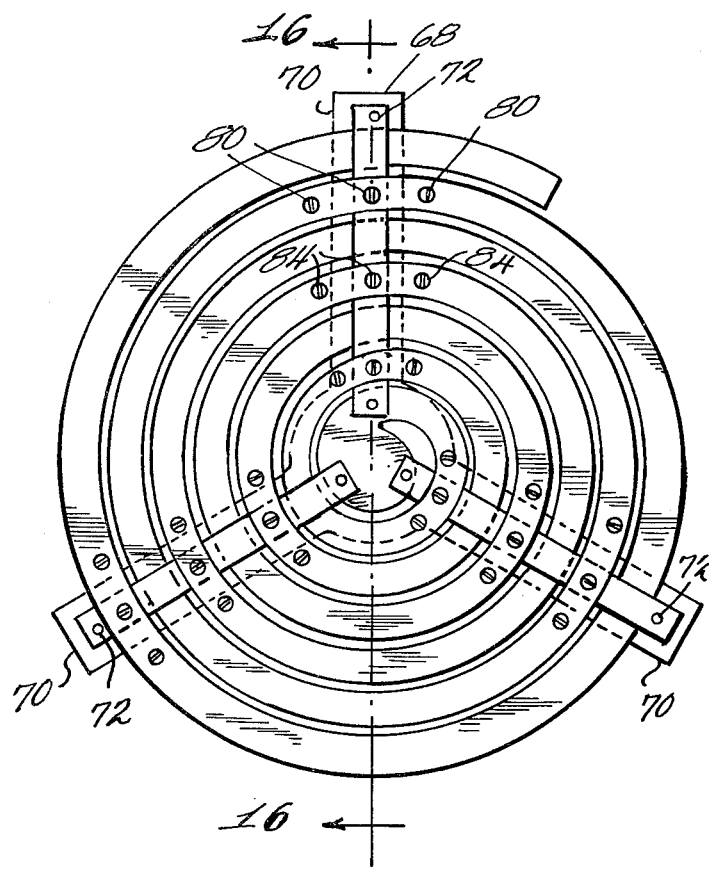
Figure 16:
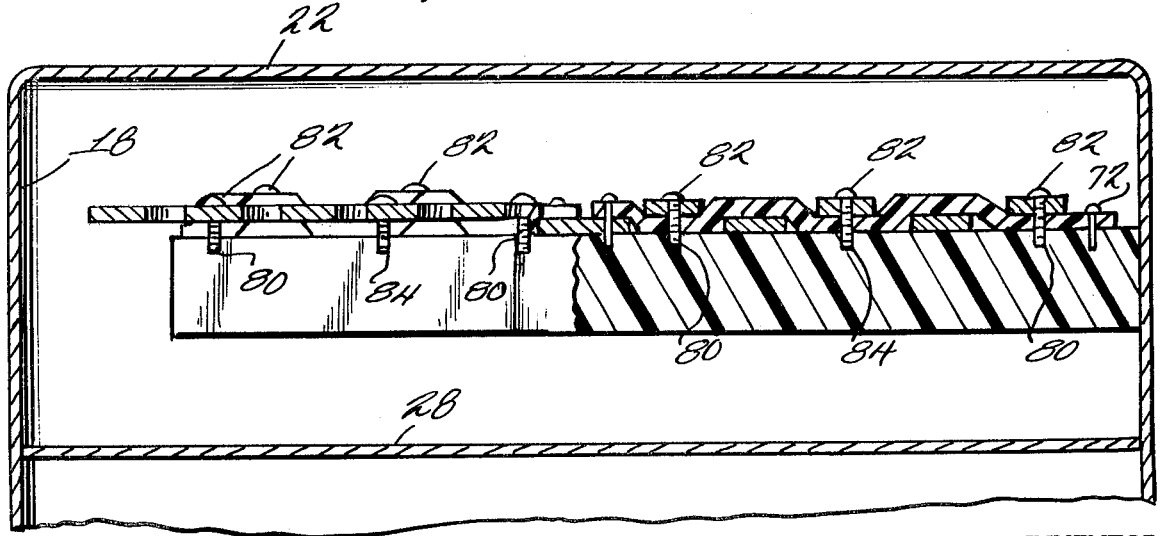

FIGS. 13 and 14 illustrate preferred modifications of the primary coil shown in FIG. 4; and FIGS. 15 and 16 illustrate top and sectional views respectively of a preferred modification of the secondary coils shown in FIGS. 3, 6, 8, and 12.

Figure 17:
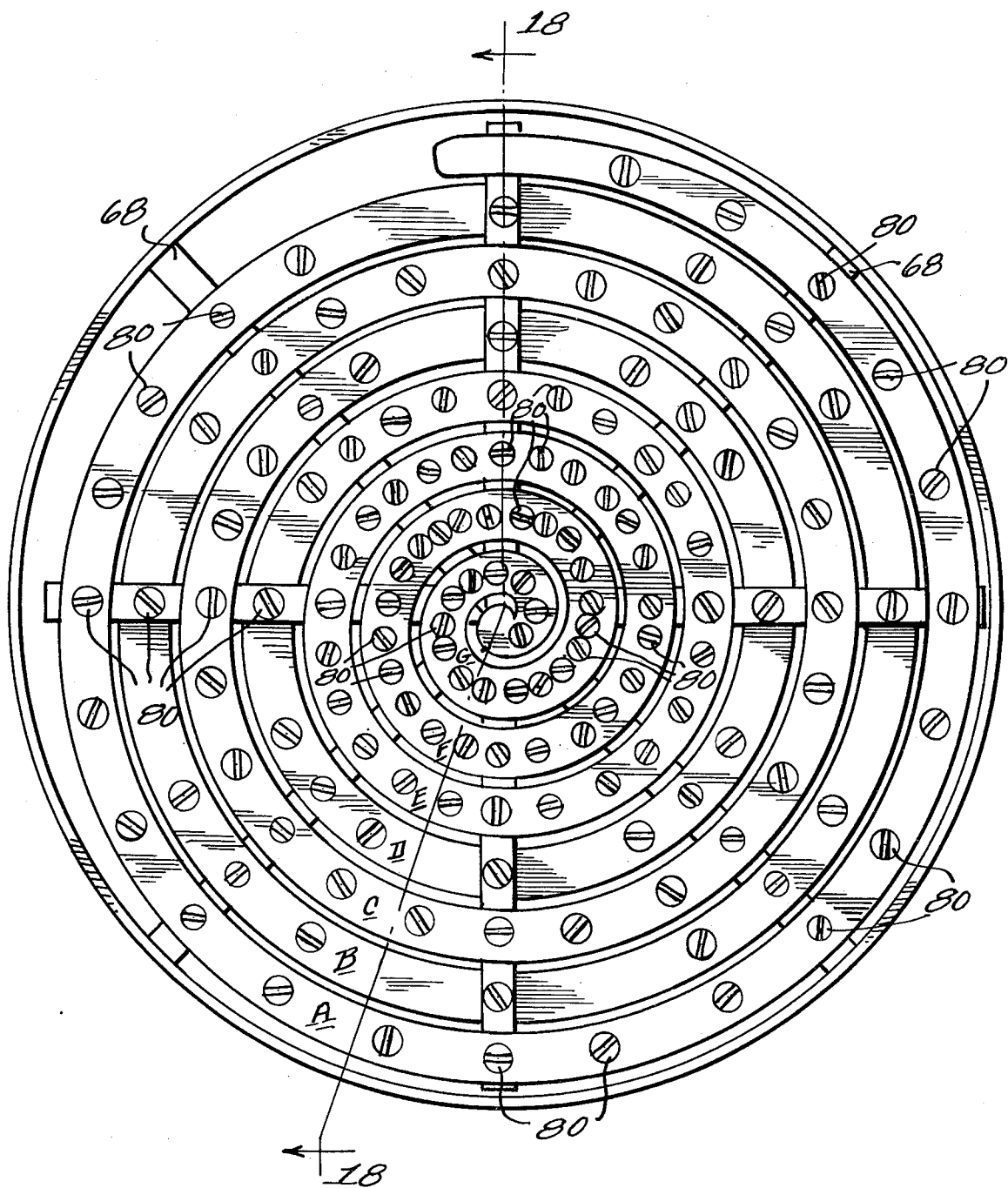
Figure 18:
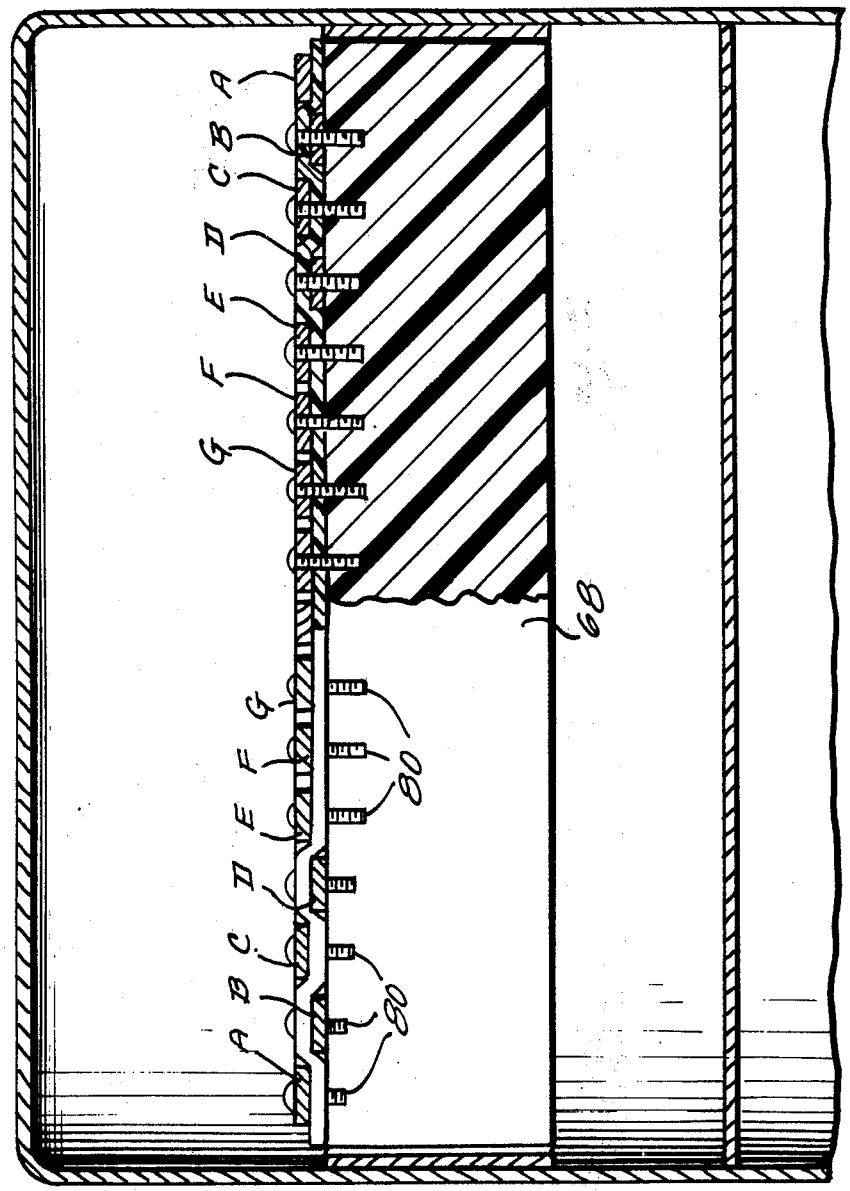
Figure 19:
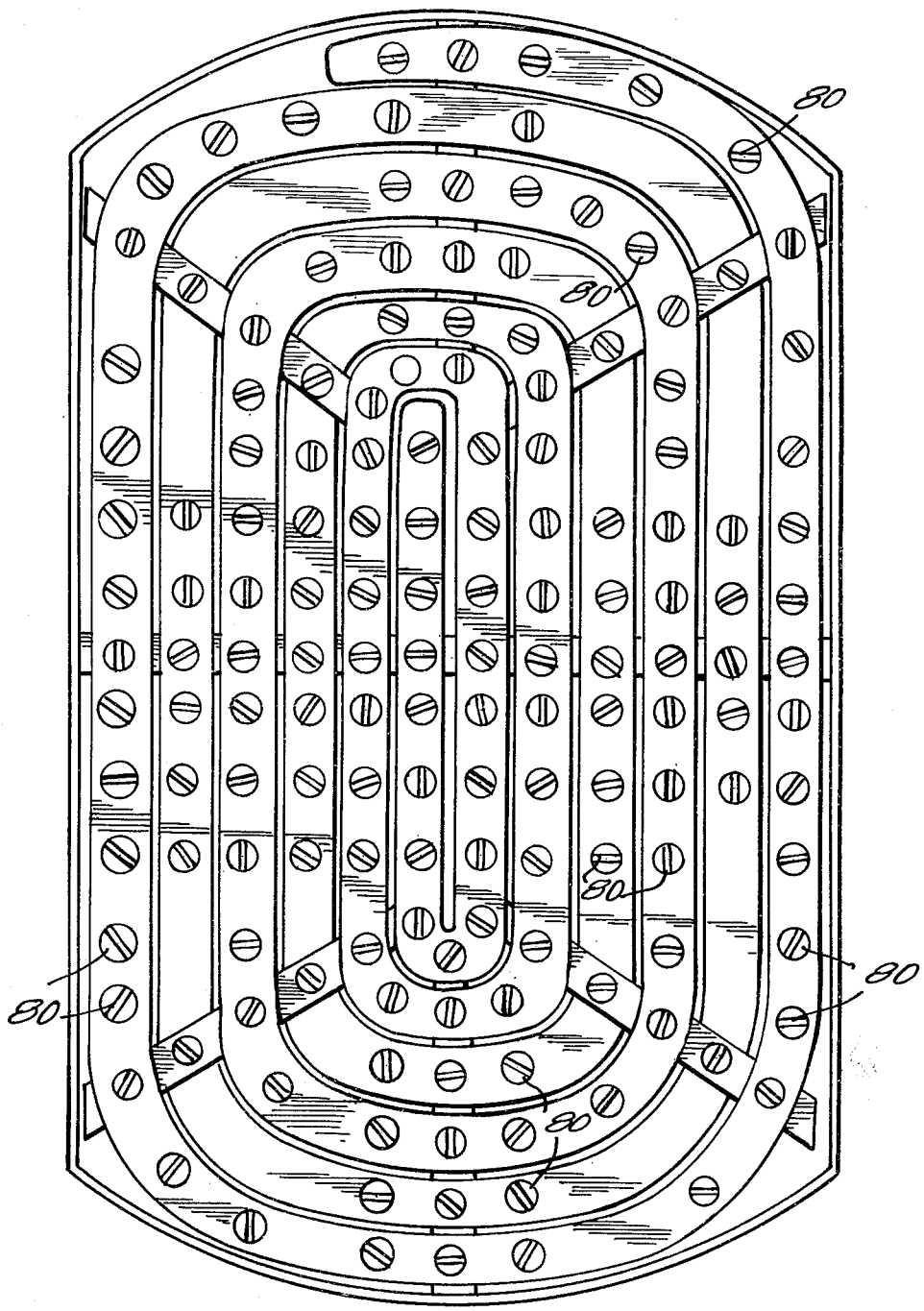

FIGS. 17 and 18 are top side sectional views of a further modification of the invention in accordance with the preferred modification shown in FIGS. 15 and 16; and FIG. 19 is a modified secondary coil embodying the principles illustrated in FIGS. 13 and 18.

Figure 1:
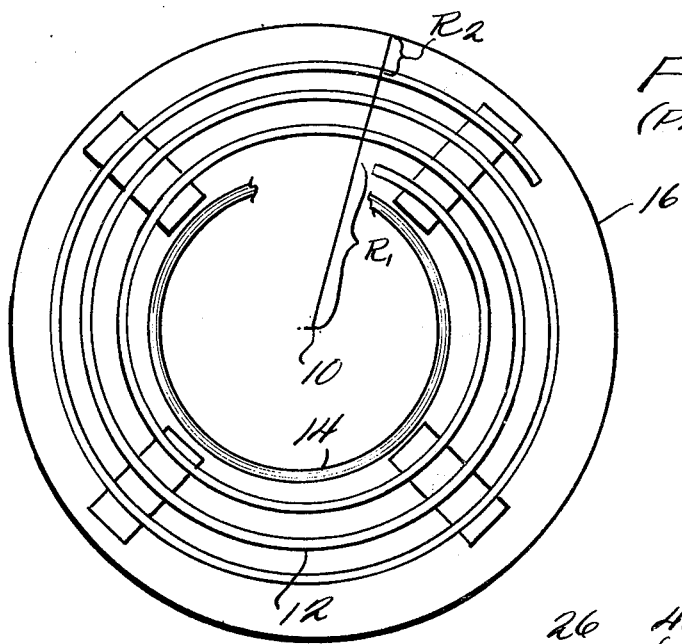

Treatment heads which have been utilized with electrotherapeutic apparatus are described and shown in U.S. Pat. Nos. 3,043,310 to A. S. Milinowski, granted July 10 1962, and 3,168,098 to W. D. Kendall et al, granted Feb. 2, 1965. Referring to FIG. 1 of the drawing, there is shown a top view of the secondary coil with respect to housing therefor as is utilized in prior art devices. The central axis 10 of the housing is perpendicular with respect to the plane of the drawing and of the secondary conductor or coil 12. The secondary coil is placed in juxtaposition with respect to the treated matter and it is the energy transferred from this coil which mainly effects the treated matter. The primary coil 14 is beneath the conductor or radiating element 12 and couples energy thereto.

The first thing to note about the secondary coil of prior art devices is the length of the distances $R_1$ and $R_2$, the distance $R_1$ being approximately 2 to 3 inches and $R_2$ being about 1 inch and the total distance from the central axis 10 to the periphery being respectively approximately 4 to 5 inches. As will be appreciated from the above dimensions, this leaves only about 1 inch of radiating or conducting surface, radially speaking or in the plane of the coil which is exposed to the treated area. Further, the conducting element forming the secondary spiral 12 is a thin conductor (approximately 1/16 inch in the plane of the coil), thereby further decreasing the radiating surface area presented to the treated matter.

Figure 2:
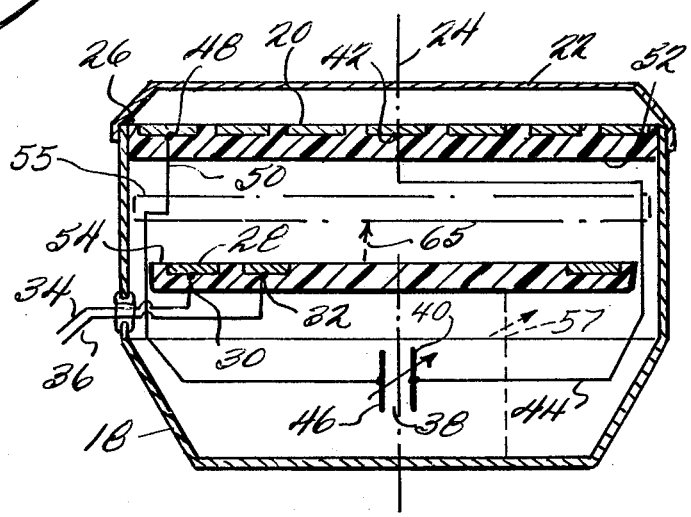
FIG. 2 is an elevation taken in section through an illustrative embodiment of an electrotherapeutic treatment head.
Figure 3:
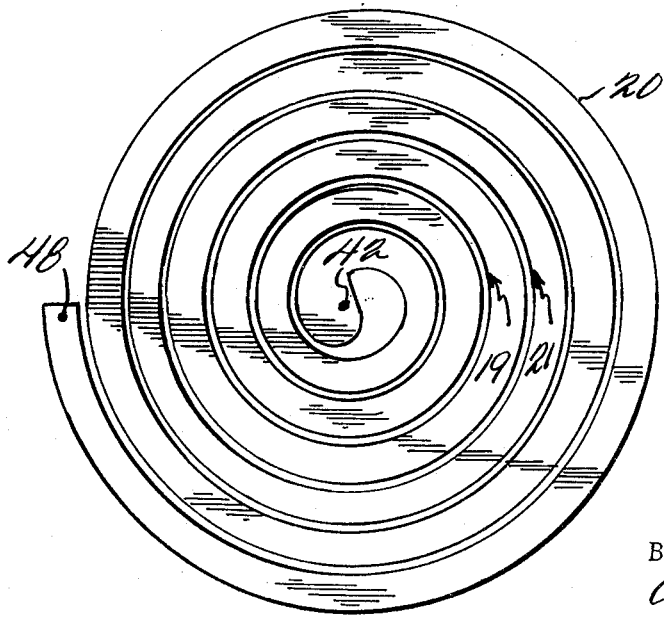
FIG. 3 is a top view of an illustrative embodiment of the conductor means or radiating coil of the treatment head.

Reference should now be made to FIGS. 2 and 3, where like reference numerals refer to the same element. The housing 18 is normally made of metallic material to insure unidirectional radiation or projection of the electrotherapeutic energy. However, it is possible to employ non-metallic materials to construct the housing 18, thereby reducing the possibility of electric shocks or radio frequency burns to the user of the treatment head.

The housing 18 is hollow and the various components comprising the electrical circuitry of the treatment head are disposed therein. The secondary conductor means or radiating element or coil 20 is located at the top of the housing 18. A dielectric covering or face plate 22 normally covers the treatment head to prevent physical contact between the treated matter and the secondary coil. Note that the secondary coil extends approximately from the central axis 24 to approximately the periphery 26 of the housing 18. Further, the conductor which forms the secondary coil spiral is substantially flat in the plane of the spiral — that is, the coil may, for example, be ¼ of an inch to 1 inch wide in the plane of the spiral. The spacing between the coil is preferably maintained at approximately 1/32 of an inch. However, this amount of spacing required can vary depending on the application. The width of the coil plus the spacing determines the pitch of the spiral, this being the distance between one point (for example, point 19 of FIG. 3) and the corresponding point on the next loop of the spiral (see point 21 of FIG. 3). The preferred pitch is approximately ½ of an inch. Since the preferred spacing is 1/32 of an inch, the preferred width of the conductor is slightly less than the preferred pitch — that is, slightly less than ½ of an inch or 15/32 of an inch. It is immediately apparent that the invention maximizes the effective contact area between the treated matter and the treatment head as is not done with the prior art devices. The coil may typically take the form of an Archimedean spiral, but it may take other forms as indicated hereinafter and as would occur to one skilled in this art.

Thus, it can be seen that the treatment head includes a housing 18 having a surface 22 adapted for placement next to the matter to be treated. Secondary conductor means 20 is substantially flat in a plane approximately parallel to the surface 22. As will be seen hereinafter, certain applications require that only a portion of the conductor means 20 be flat in the parallel plane.

Disposed below the secondary coil is the primary coil 28 which is shown in top view in FIG. 4, the primary coil preferably being a loop with its center approximately at the axis 24. The primary coil is also preferably, although not necessarily, a flat conductor as is the secondary coil. Further, it is desirable to feed the energy from the electrotherapeutic circuit to the terminals 30 and 32 as shown in FIGS. 2 and 4 — that is, it is desirable, although not necessary, to have these terminals side by side, thereby effectively maintaining a primary coil of constant width around its circumference, that is, the coil broadens or thickens as it moves away from its feed points whereas the combined width of the two coils (the two ends of the loop) are approximately equal in width to the conductor portion at the opposite side of the loop. It is further possible in given situations to employ a primary coil which spirals as the secondary. The wires 34 and 36 are inputs from the electrotherapeutic drive circuit and the pulsed energy is delivered over these wires to the primary coil 28.

Reference should now be made to FIG. 13, which shows an improved, preferred primary coil 28 for use with the embodiment of this invention shown in FIG. 2. As can be seen from comparing FIGS. 3 and 13, the surface area of the coil 28 is directed towards a substantial fraction of the surface area of the coil 20. Typically, the radius of the coil 20 in FIG. 3 from axis 42 to terminal 48 is 4 to 5 inches. The width of the coil 28 at the widest point typically approximates 3 inches. Of course, the above dimensions are given for purposes of illustration only and substantial variations therefrom are well within the scope of one having ordinary skill in this art. When the primary coil 28 of FIG. 13 is compared with the typical prior art, primary coil having approximately a one-eighth inch width, it is apparent that the area of the secondary coil 20 directly exposed to the primary coil 28 is substantially increased. Thus, the coupling of electromagnetic energy from the therapeutic drive circuit through the primary coil to the secondary coil is substantially increased, thereby further resulting in the improved performance of this invention. Preferably, primary coil 28 is flat in a plane parallel to the plane of secondary coil 20 and is disposed below it. Of course, it may be desirable in some applications to provide a primary coil 28 having a surface area larger than that of secondary coil 20. The important thing is to provide a primary coil of sufficiently large surface area with respect to the surface area of the secondary coil so as to insure maximum coupling of electromagnetic energy from the primary to the secondary.

Returning to FIG. 3, tuning or adjustable condenser 38 is also enclosed within the housing 18 although not necessarily so. In other words, the condenser 38 may be placed outside the treatment head if so desired; for example, within a treatment head support art (not shown) containing the wires 34 and 36 and extending from the housing for the electrotherapeutic drive circuit. The condenser 38 is normally tunable through a control knob (not shown) which would be placed somewhere on the outside of the housing 18 to provide the proper adjustment. The purpose of the tuning of condenser 38 is to effectuate a maximum transfer of energy to the treated matter, taking into consideration that the matter loads the secondary circuit. Plate 40 of condenser 38 is connected approximately at the center 42 of the secondary spiral coil by wire 44, the center 42 being approximately at the axis 24 of the housing 18. The plate 46 of condenser 38 is connected approximately at the outermost portion 48 of the secondary spiral coil by wire 50. Although condenser 38 has been shown as a two-plate condenser, it would, of course, be a matter of mere expediency for one skilled in this art to employ a multiplate condenser if it were so warranted by a particular situation.

The secondary and primary coils may be respectively mounted on dielectric laminates 52 and 54. These laminates may be peripherally supported at the periphery of housing 18 — the supporting mechanism not being shown as it is not important to the invention.

Reference should now be made to FIG. 5 which is an electrical schematic showing the various relations of the components used in the treatment head. The electrotherapeutic drive circuit 56 is connected directly to the primary 28. A typical operating frequency for the drive circuit is 27.12 mc. It is to be understood that all preferred dimensions given are based on the above frequency. Therefore, if the operating frequency changes, corresponding changes may take place in some or all of the preferred dimensions. A coupling condenser 58 may be connected in series with the primary to provide D.C. isolation of the primary from the drive apparatus. The secondary coil 20 is connected in series with the adjustable condenser 38 by wires 44 and 50.

Reference should now be made to FIG. 6 which shows another illustrative embodiment of the invention where the flat conductors or radiation elements of the secondary spiral from a central point corresponding to axis 24 of the housing 18 and terminate at a point 60 intermediate to the central axis 24 and the periphery 26 at the housing 18. The spiral of the secondary coil is completed to a point closer to the periphery of housing 18 than the termination point of the conductor 20 by a substantially thinner conductor or further conductor means 62 which may be solid or tubular. A tubular conductor is shown in FIG. 6A, which is a cross-section taken along the line 6A—6A of FIG. 6. As can be seen from FIG. 6, a further way to looking at the difference between conductors 20 and 62 is to note that conductor 20 is substantially flat in the plane of the spiral while conductor 62 is not. The conductor 62 is preferably ⅛ of an inch wide, other variations, of course, being possible. This particular arrangement provides increased benefits when it is desirable to concentrate the output energy from the drive apparatus toward the center of the treatment head — for example, when the hand or wrist is being treated. It is not always necessary that the spiral extend completely to the periphery as is indicated by the termination of conductor 62 at a point 63 removed from the periphery. The important thing, especially when treating a small area, is to extend the spiral inwardly to the area around the axis 24.

Another variation of the secondary arrangement is diagrammatically shown in FIG. 12, where the arrangement of FIG. 6 is reversed — that is, the further conductor means 65 is substantially wider than the conductor means 67 which commences spiralling from a point approximately at the axis of the housing.

Referring to FIG. 7, there is shown a compact treatment head which includes the same electrical components as described in the treatment head of FIG. 2. However, these components are now arranged in a more compact fashion thereby resulting in treatment head which facilitates manipulation thereof by the patient or apparatus operator. Particularly, the secondary coil 20 and the primary coil 28 are mounted on opposite sides of a common dielectric laminate or sheet 64. Conductors 20 and 28 may be stamped from sheet metal and screwed to the sheet 64 or they may be painted, sprayed or printed on or embedded on the dielectrical sheet 64 or mounted on stand-off insulators.

Of course, by mounting coils 20 and 28 on a common mounting board, there is no capability of varying the distance between the primary and secondary coils. However, in FIG. 2 provision may be made to vary the distance (as is diagrammatically indicated by the dotted lines 54 and dotted arrow 65 representing the coil 28 when it is adjusted to another position) between the secondary coil 20 and primary coil 28 by any known expedient, which is diagrammatically shown at 57 in FIG. 2. For example, the distance between the coils may be varied in the same manner as the distance between plates of condenser 38 is varied, this being shown in the two abovementioned patents to Milinowski and Kendall et al. When the distance between the primary and secondary coils is varied, it has been found that best results are generally obtained when the gap is approximately 13/16 inches wide. It is obvious that for certain applications, this distance is not optimum and therefore deviations therefrom will depend on the application. Of course, it is the relative movement between the secondary and primary coils that is important. Therefore, the secondary could be moved with respect to the primary or both could be moved as long as there is relative movement between them.

To further facilitate the compactness of the treatment head shown in FIG. 7, condenser 38 may be oriented with its two plates parallel to the planes of the coils 20 and 28. Normally, this would give rise to eddy currents and other undesirable effects at the primary and secondary coils. However, this undesirable interaction may be significantly reduced by insertion of an insulating plate 66 between the condenser 38 and the coils 20 and 28. As can be seen, the condenser 38 is so oriented that it can be most compactly enclosed within the housing 18.

FIG. 8 shows an oblong-shaped secondary coil 67. This shape of secondary coil is incorporated into a housing having a corresponding oblong or rectangular shape (not shown). The use of an oblong-shaped treatment head has been particularly advantageous when hard-to-reach areas are treated. For instance, the treatment of the side of the neck is particularly awkward and inefficient when prior art treatment heads are employed. This is because these treatment heads are typically circular in shape and have diameters of approximately 9 to 10 inches. However, the typical preferred dimensions of the secondary coil or conductor means 67 shown in FIG. 8 are 8 to 9 inches long and 5 to 6 inches wide. It has been found that these particular dimensions are generally satisfactory for delivering sufficient energy to the treated area since the treatment head may be placed relatively close to the treated area — in particular, when the treated area is a hard-to-reach spot such as the side of the neck or elbow.

Referring to FIGS. 9 and 10, a description will now be given of an illustrative embodiment of a support mechanism for the secondary coil. Like reference numerals, respectively, refer to the same elements. The conductor elements of the secondary coil are indicated by the numeral 20 in FIG. 10. A plurality of webs or interleaving support members are placed alternately above and below sucessive conductor elements of the secondary coil 20 with respect to a changing distance from the axis of the housing means as shown in FIG. 10. In FIG. 9 there are shown three webs 68 which interleave the coil 20. The webs and coil 20 are mounted on support 70 as shown in FIG. 9. Support 70 may have the same general shape as the shape established by the webs 68 or may take a solid shape. In FIG. 10, for example, the webs 68 are placed 120° apart and, therefore, the webs together with the support 70 have the general form of three spokes spaced 120° apart around a common center.

The interleaving support mechanism for the secondary coil 20 is particularly advantageous because it permits the coil to be securely mounted to the base 70 while at the same time increasing the effectiveness of the treatment head. In prior approaches to the problem of securing the secondary coil 20 to the support 70, the coil has been fastened to the support 70 each time the coil crossed over a spoke of the support as the coil spiralled outwardly. The necessity for this has been overcome by providing an interleaving support or web for the coil 20, the web being connected at opposite ends thereof to the base 70 by fasteners 72 as indicated in FIG. 10. Further, the interleaving of the web 68 with the coil 20 causes the coil to have an undulating shape as the coil spirals outwardly. As pointed out before, it has been observed that effectiveness of the treatment head is increased because of the undulating shape of the secondary coil. The webs 68 are fixedly positioned with respect to the housing by connecting the support 70 to the housing. The support 70 could, of course, be connected to the periphery of the housing 18 in any of many known ways. For instance, a screw (not shown) through the housing may connect the ends 74 of the support 70 to the housing. The webs 68 and support member 70 are preferably made of a flexible, thermosetting resin, such as Teflon. Of course, the webs 68 and support member 70 may be made of other suitable materials so long as they are sufficiently rigid, to provide the required support of secondary coil 20.

Although only three webs 68 are shown in FIG. 9, the number of webs may be varied depending on the particular application. For example, in FIG. 11 seven webs for supporting the secondary coil of an oblong treatment head are diagrammatically shown.

Although the number of webs used to suport the secondary coil may be varied, this number should be odd whenever the secondary coil is disposed over and under successive webs 68 over the entire length of the coil. However, as will be brought out in more detail with respect to FIGS. 17, 18, and 19, the number of webs should preferably be even if the particular application so requires. The reason for keeping the number of webs odd whenever the secondary coil is disposed over and under the webs over the entire length of the coil will be apparent after considering FIG. 9. Note at point *a* that the conductor 20 travels beneath the web 68. As the conductor spirals inwardly, the conductor 20 moves over the next web 68 at point *b*. At point *c*, the conductor 20 moves under the following web 68. As the coil 20 continues to spiral inwardly, it will move over and under the webs 68. This will insure the required undulating arrangement of the secondary coil while at the same time providing a strong support for the coil. That is, if an even number of webs were employed, then for a given web 68 the coil 20 will pass over that web each time that web is encountered as the coil spirals inwardly. However, note FIG. 9 at points *a*, *d* and *e*. Here the coil 20 goes under the web 68 at point *a*, over at point *d*, under at point *e*, and so forth. This insures a strong mechanical support while at the same time providing the undulating arrangement required for increased effectiveness of the treatment head.

Since the spacing between the adjacent conductors of coil 20 may be quite small and since the treatment head may be subject to rough handling, it is absolutely necessary that a strong mechanical support be provided for the coil 20 to prevent the possibility of one conductor of the coil 20 shorting with an adjacent conductor and thereby decrease the effectiveness of the treatment head. The necessary support has been provided by the unique arrangement taught in FIGS. 9–11. The primary coil (not shown) may be mounted on the lower side of the support 70 or else may be movably disposed with respect to the secondary coil 20 as described hereinbefore.

Figure 11:
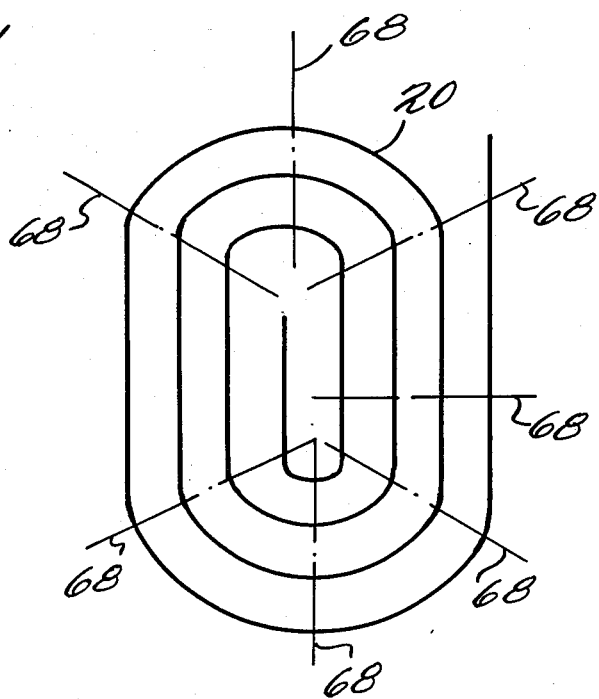
FIG. 11 is a top view of a preferred embodiment of the structure shown in FIGS. 9 and 10.

Referring to FIG. 14, there is shown an oblong primary coil having the same dimensional relationship to the oblong secondary coil shown in FIG. 11 as the primary coil shown in FIG. 13 has to the secondary coil shown in FIG. 3. Thus, the advantages described hereinbefore for the primary coil 28 shown in FIG. 13 are also available with the FIG. 14 primary coil.

Thus, there has now been described support means (housing 18) having a central or other convenient axis, said housing supporting and enclosing a plurality of electrical components (primary coil 28 and secondary coil 20 and tuning condenser 38), said electric components providing means for transferring energy from an electrotherapeutic drive circuit to treated matter or organic tissue. The secondary coil is normally placed in juxtaposition with respect to the human body, said secondary coil being flat in the spiral of the coil, said spiral extending outwardly from approximately at the said axis. The primary coil is preferably also a flat conductor in the plane of its loop or spiral around the said axis. By providing the flat secondary coil which extends approximately from the axis to a point either approximately at the periphery of the housing 18 or to a point intermediate the axis in the periphery, maximum depth of penetration or effective treatment at deeper levels is provided while at the same time reducing the undesired side effects of undue heating of the tissue.

Further, means have been described for providing a compact treatment head which provides for (1) mounting the primary and secondary coils on opposite sides of a common dielectrical sheet and (2) orienting the plates of the condenser 38 parallel to the plane of said coils, an electrical shield being placed between the coils and condenser.

Although the drawing shows the secondary coil taking the form of a spiral having a constant width, a spiral having a gradually widening strip extending either outwardly or inwardly would also fall within the scope of the invention.

It has also been observed that when the primary coil spirals outwardly in a clockwise direction, good results are generally obtained when the secondary coil spirals outwardly in a counterclockwise direction. Further, it has been observed that beneficial results are generally obtained when the outer end of the secondary spiral is in the same radial plane as the outer end of the primary coil, that is, the terminals 30 and 32 of the primary coil should be preferably located approximately beneath the terminal 48 of the secondary, as is indicated in FIG. 2.

The preferred thickness of the secondary coil is 0.049 inches and of the primary coil is 0.033 inches. Of course, these dimensions can be adjusted to suit the needs of the particular situation. Basically, these conductors must be of sufficient capacity to carry the current at the operating frequency. At the same time, they must have sufficient mechanical strength to maintain rigidity. Further, desirable thickness will vary with material, finish, and strength.

It is further within the scope of the invention to use a single turn of wire for the primary coil, although it has been found that generally better results occur when the primary turn is a flat coil, as shown in FIGS. 4, 13, or 14.

Referring to FIG. 15, there is shown a top view of a preferred embodiment of the secondary coil shown in FIG. 3. In FIG. 16, there is shown a cross-sectional view of the secondary coil shown in FIG. 15, the cross-section being taken on line 16—16.

Referring to FIG. 15, there are shown a plurality of bolts or protuberances 80 connected through the secondary coil 20. The heads 82 of the bolts 80 are directed toward the surface 22 of the housing 18, as shown in FIG. 16. The housing 18, surface 22 and primary 28 are diagrammatically indicated in FIG. 16.

The bolts 80 may be disposed in groups periodically spaced along the length of the spiral secondary coil 20, as shown in FIG. 15. Further, the periodically spaced groups of bolts or protuberances 80 are disposed at the intersections of the webs or interleaving support members 68 with the spiral secondary 20. Further, the bolts 80 may be placed at the intersections where the interleaving support members 68 pass above the spiral secondary 20.

As shown in FIG. 15, there may be three bolts 80 in each of the periodically spaced groups. Broadly speaking, the invention described thus far with respect to FIGS. 15 and 16 encompasses the use of a plurality of protuberances disposed on the flat surface of a flat secondary coil as described hereinbefore with respect to FIG. 3 for example. As shown in FIG. 16, the heads of the bolts 80 correspond to the protuberances. However, it would be obvious to others having ordinary skill in this art to devise other means for providing the desired protuberances.

Referring to FIG. 15, it should be noted that the slots 84 in the heads of the bolts 80 are directed approximately towards the center axis of the coil 20. This modification is also preferred when bolt heads are employed as protuberances.

Referring to FIG. 16, the bolts 80 which do not connect with the support 70 extend beyond the webs 68 by a substantial distance, this distance being preferably 3/16 to ¼ of one inch. Thus, broadly speaking, it has been found preferable to provide bolts 80, the length of which extends substantially beyond the surface of the spiral coil 20 and away from the surface 22 of the housing 18 and towards the primary coil 28.

Referring to FIGS. 17 and 18, there is shown a preferred modified embodiment of the secondary coil shown in FIGS. 15 and 16. As shown in FIG. 18, the bolts 80 are shorter at the outer portion comprising turns A and B than they are at middle turns C and D while the bolts 80 through middle inner turns D and C are shorter than the bolts 80 extending through inner turns E, F, and G. For example, the length of the bolts 80 through outer turns A and B may be ¼ inch, while the bolts through turns C and D may be ⅜ inch long and the bolts through inner turns E, F, and G may be ½ inch long. Thus, broadly speaking, the outer one-third of the secondary coil turns has bolts of a first length extending therethrough while the middle one-third of the secondary coil turns has bolts extending therethrough of a second length which is longer than the length of the bolts through the outer third of the secondary and the inner one-third of the spiral turns has bolts extending therethrough of a third length which is longer than the length of the bolts through either the outer or middle portions of the secondary coil. By locating the longer bolts at the inner portion of the secondary spiral and decreasing the length of these bolts toward the outer portion of the secondary spiral, the resulting energy pattern radiated by the coil is more intensified at the area adjacent the center of the secondary coil than it is at the area adjacent the outer portion of the coil. Of course, it would be obvious to one having ordinary skill in this art to vary the locations of the bolts of different length and thereby obtain a particular radiation pattern. Thus, in some applications, it may be desirable to have the lengths of the bolts 80 increase in length from the inner to outer portions of the secondary coil.

It can be seen that the number of bolts or protuberances of the secondary coil are substantially increased with respect to that shown in FIG. 15, thereby increasing the efficacy of the radiation pattern in some applications. Preferably, the arrangement of bolts through the secondary coil, as shown in FIG. 17, is established as follows: first, the bolts on outer coil A are located preferably 1 inch from the central line of the webs 68; and, second, with these bolts so located on outer coil A, the remaining bolts of turns B through G are located on radial lines respectively directed from each of the bolts 80 on outer turn A to the center of the spiral.

In the embodiment of the invention shown in FIG. 9, the spiral turns are disposed above and below successive adjacent webs 68 over the entire length of the spiral. However, for some applications, it has been found desirable to dispose all of the inner turns (for example, turns E, F, and G) of the spiral secondary in a flat plane above the support members 68 while outer turn A is disposed above all of the webs 68 while turn B is disposed above and below successive adjacent turns. Turn C, like turn A, is disposed above all the webs while turn D, like turn B, is disposed above and below successive adjacent turns, see FIG. 17. As will be apparent to those having ordinary skill in this art, the disposition of the turns of the spiral in relation to the webs 68 may be varied depending on the particular application. In one preferred embodiment of the invention, the three outer turns of the spiral are disposed as shown in FIG. 17 while all the remaining inner coils are disposed above the webs 68.

As has been stated hereinbefore with respect to embodiment of the invention shown in FIG. 9, the number of webs 68 is preferably odd when the coil is disposed above and below successive adjacent webs over the entire length of the coil. However, in the embodiment shown in FIGS. 17 and 18, the number should be even. Thus, in the embodiment of FIG. 17, the number of webs 68 is eight, thereby lending itself to a symmetrical distribution of the protuberances 80 around the secondary spiral coil.

FIG. 19 embodies the same principles as those described for the embodiment of FIGS. 17 and 18 with the exception that an oblong-shaped spiral is employed. With this particular shape, the even number of interleaving support members is particularly appropriate.

Although several embodiments of the present invention, together with various modifications thereof, have been herein shown and described, it is to be understood that still further modifications thereof may be made without departing from the spirit and scope of the appended claims.

What is claimed is:

1. A treatment head utilizing electromagnetic energy delivered from an electrotherapeutic drive circuit for electrotherapeutically applying said energy to organic matter comprising a hollow housing including a support means;
    conducting and radiating means for transferring said electromagnetic energy to said matter, said conducting and radiating means being mounted within said housing means and spiraling in one place around an axis approximately from said axis to a point located not farther away from said axis than the periphery of said housing means, at least a portion of the conducting and radiating means being substantially flat in the plane of the spiral, the width in the plane of the spiral of at least part of said conducting and radiating means being greater than half the pitch of said conducting and radiating means;
    a primary coil connected to said drive circuit for coupling said energy to said conducting and radiating means, said primary coil having a loop-shape and being flat in the plane of its loop and substantially parallel to spiral-shaped conducting and radiating means; and
    means for adjusting and spacing between said conducting and radiating means and said primary coil.

2. A treatment head as in claim 1 where the spacing between said flat conductor means and said primary coil is approximately ½ of an inch.

3. A treatment head utilizing electromagnetic energy delivered from an electrotherapeutic drive circuit for electrotherapeutically applying said energy to organic matter comprising a hollow housing including a support means;
    conducting and radiating means for transferring said electromagnetic energy to said matter, said conducting and radiating means being mounted within said housing means and spiraling in one place around an axis approximately from said axis to a point located not farther away from said axis than the periphery of said housing means, at least a portion of the conducting and radiating means being substantially flat in the plane of the spiral, the width in the plane of the spiral of at least part of said conducting and radiating means being greater than half the pitch of said conducting and radiating means;

a primary coil connnected to said drive circuit for coupling said energy to said conducting and radiating means, said primary coil having a loop-shape and being flat in the plane of its loop and substantially parallel to spiral-shaped conducting and radiating means; and a plurality of interleaving support members, said interleaving support members being fixedly positioned with respect to said housing and being placed alternately above and below successive conductor elements of the said conducting and radiating means with respect to a changing distance from said axis of said housing means, the number of said interleaving support members being odd thereby causing the said conducting and radiating means to have an undulating shape.

4. A treatment head as in claim 1 including a further support member fastened to said housing, said conductor means and interleaving support member being mounted upon said further support member, and where said interleaving support members take the form of a plurality of spokes spaced apart around said axis of the housing means.

5. A treatment head as in claim 1 where the number of said interleaving support members is seven.

6. A treatment head utilizing electromagnetic energy delivered from an electrotherapeutic drive circuit for electrotherapeutically applying said energy to organic matter comprising a hollow housing including a support means;

conducting and radiating means for transferring said electromagnetic energy to said matter, said conducting and radiating means being mounted within said housing means and spiraling in one place around an axis approximately from said axis to a point located not farther away from said axis than the periphery of said housing means, at least a portion of the conducting and radiating means being substantially flat in the plane of the spiral, the width in the plane of the spiral of at least part of said conducting and radiating means being greater than half the pitch of said conducting and radiating means;

a primary coil connected to said drive circuit for coupling said energy to said conducting and radiating means, said primary coil having a loop-shape and being flat in the plane of its loop and substantially parallel to spiral-shaped conducting and radiating means;

where said conductor means includes a plurality of protuberances (1) disposed on the flat surface of said electrical conductor means, (2) directed toward the said surface of the housing, and (3) disposed in groups periodically spaced along the length of the said spiral-shaped conductor means; and a plurality of interleaving support members, said interleaving support members being fixedly positioned with respect to said housing and being disposed alternately above and below successive conductor elements of the said spiral-shaped conductor means.

7. A treatment head as in claim 6 where said periodically spaced groups of protuberances are disposed at the intersections of the said interleaving support members with said spiral-shaped conductor means.

8. A treatment head as in claim 7 where said groups of protuberances are disposed at the intersections where the said interleaving support members pass above the said spiral-shaped conductor means.

9. A treatment head as in claim 8 where there are three bolts per group.

10. A treatment head as in claim 8 including a plurality of bolts connected through said conductor means, the heads of said bolts corresponding to the said protuberances.

11. A treatment head as in claim 10 where said housing has a substantial center axis and where the slots in the said heads of said bolts are directed approximately towards the said center axis.

12. A treatment head as in claim 9 where the length of said bolts extends substantially beyond the surface of said flat conductor means and away from the said surface of the housing.

13. A treatment head utilizing electromagnetic energy delivered from an electrotherapeutic drive circuit for electrotherapeutically applying said energy to organic matter comprising a hollow housing including a support means;

conducting and radiating means for transferring said electromagnetic energy to said matter, said conducting and radiating means being mounted within said housing means and spiraling in one place around an axis approximately from said axis to a point located not farther away from said axis than the periphery of said housing means, at least a portion of the conducting and radiating means being substantially flat in the plane of the spiral, the width in the plane of the spiral of at least part of said conducting and radiating means being greater than half the pitch of said conducting and radiating means;

a primary coil connected to said drive circuit for coupling said energy to said conducting and radiating means, said primary coil having a loop-shape and being flat in the plane of its loop and substantially parallel to spiral-shaped conducting and radiating means;

where said conductor means includes a plurality of protuberances disposed on the flat surface of said electrical conductor means and where said protuberances include a plurality of bolts or the like, the heads of said bolts being directed toward the surface of the housing, and the shafts of said bolts extending through said conductor means, the bolts located at the center portion of said conductor means being of different length than the bolts at the outer portion of said conductor means, thereby causing the intensity of the radiation adjacent the center portion to be different from the intensity of the radiation at the outer portion; and a plurality of webs radially extending from the center of said spiral, the said center portion of said conductor means being disposed entirely above said webs.

14. A treatment head, as in claim 13, where the three outer turns of said spiral shaped conductor means are disposed above and below the said webs.

15. A treatment head, as in claim 14, where the outer coil of said spiral shaped conductor means is disposed entirely above all of said webs, the second outermost turn of said spiral shaped conductor is disposed above or below successive adjacent webs and the third outermost turn is disposed entirely above all of the said webs.

* * * * *